United States Patent [19]

Maione et al.

[11] Patent Number: 5,284,827
[45] Date of Patent: Feb. 8, 1994

[54] SYSTEMIC TREATMENT OF METASTATIC CANCER WITH PLATELET FACTOR 4

[75] Inventors: Theodore Maione, Wakefield; Richard J. Sharpe, Newton, both of Mass.

[73] Assignee: Repligen Corporation, Cambridge, Mass.

[21] Appl. No.: 600,472

[22] Filed: Oct. 19, 1990

Related U.S. Application Data

[60] Division of Ser. No. 451,021, Dec. 27, 1989, abandoned, which is a continuation-in-part of Ser. No. 295,955, Jan. 10, 1989, abandoned.

[51] Int. Cl.⁵ .................... A61K 37/02; A61K 35/14
[52] U.S. Cl. .......................................... 514/12; 424/88; 435/69.6; 514/2; 530/324; 530/380
[58] Field of Search ................. 424/532, 94.1; 514/2, 514/12; 530/350, 380, 300, 327, 324, 380; 435/69.6

[56] References Cited

U.S. PATENT DOCUMENTS 4,645,828  2/1987  Twardzik .............................. 530/324
5,086,164  2/1992  Malone et al. ....................... 530/324

OTHER PUBLICATIONS

Folkman, J. et al. 1983 Ciba Found Sympos. 100: 132–49. "The role of heparin in angiogenesis."

Primary Examiner—Christine M. Nucker
Assistant Examiner—T. Cummingham
Attorney, Agent, or Firm—Saliwanchik & Saliwanchik

[57] ABSTRACT

The subject invention concerns a novel treatment for cancer. Specifically, the invention concerns the systemic administration of recombinant Platelet Factor Four (rPF4) to inhibit tumor growth in a mammal having metastatic cancer.

4 Claims, 12 Drawing Sheets

Figure 1A

```
 BclI HindIII
↓GAT CAA GCT TCT ATG GAA GCT GAA GAA GAC
  TT CGA AGA TAC CTT CGA CTT CTT CTG
      ↑
              Met Glu Ala Glu Glu Asp BstEII
↓GGT GAC CTG CAG TGC CTG TGC GTT AAA ACT
 CCA CTG GAC GTC ACG GAC ACG CAA TTT TGA
        ↑
 Gly Asp Leu Gln Cys Leu Cys Val Lys Thr EagI
         ↓                      ↓
 ACT TCT CAG GTT CGG CCG CGT CAT ATC ACT
 TGA AGA GTC CAA GCC GGC GCA GTA TAG TGA
                     ↑
 Thr Ser Gln Val Arg Pro Arg His Ilu Thr
```

Figure 1B

```
AGT CTG GAA GTT ATC AAA GCT GGT CCG CAT
TCA GAC CTT CAA TAG TTT CGA CCA GGC GTA
Ser Leu Glu Val Ilu Lys Ala Gly Pro His

EspI
                    ↓
TGC CCG ACT GCT CAG CTG ATC GCT ACT CTG
ACG GGC TGA CGA GTC GAC TAG CGA TGA GAC
Cys Pro Thr Ala Gln Leu Ilu Ala Thr Leu

AAA AAC GGT CGT AAA ATC TGC CTG GAC CTG
TTT TTG CCA GCA TTT TAG ACG GAC CTG GAC
Lys Asn Gly Arg Lys Ilu Cys Leu Asp Leu
```

Figure 1C

```
       BbeI↓
CAG GCG CCG CTG TAC AAA AAA ATC ATC AAA
GTC↑CGC GGC GAC ATG TTT TTT TAG TAG TTT
Gln Ala Pro Leu Tyr Lys Lys Ilu Ilu Lys

SmaI
                           ↓
AAA CTG CTG GAA TCC TGA TCC GGT ACC CGG
TTT GAC GAC CTT AGG ACT AGG CCA TGG↑GCC
Lys Leu Leu Glu Ser  *

SacI↓
GAG CTC
C↑
```

SYSTEMIC TREATMENT OF METASTATIC CANCER WITH PLATELET FACTOR 4

This is a division, application Ser. No. 07/451,021, filed Dec. 27, 1989, which is a continuation-in-part of co-pending application Ser. No. 295,955; filed Jan. 10, 1989 both now abandoned.

BACKGROUND OF THE INVENTION

Angiogenesis, the development of new capillary blood vessels, is an important process in the developing fetus and growing human. However, in healthy adults, angiogenesis occurs significantly only during wound healing and in the menstrual cycle.

It is now widely recognized that much of the angiogenic activity occurring in adults is pathological in nature. For example, proliferation of vascular endothelial cells and formation of new capillaries is essential for growth of solid tumors beyond a few cubic millimeters in volume (Folkman et al. [1983] Ciba Found. Symp. 100:132-149). We now understand that developing tumors secrete growth factors which stimulate neighboring endothelial cells to divide and migrate toward the tumor.

In addition to growth of solid tumors, other conditions involving angiogenic dysfunctions include diabetic retinopathy, retrolental fibroplasia, neovascular glaucoma, psoriasis, angiofibromas, immune and non-immune inflammation (including rheumatoid arthritis), capillary proliferation within atherosclerotic plaques, hemangiomas, and Kaposi's Sarcoma have also recently been recognized as diseases possessing characteristics of dysregulated endothelial cell division and capillary growth. These conditions along with growth of solid tumors are collectively referred to as "angiogenic diseases" (Folkman, J., and M. Klagsbrun [1987] Science 235:442-447).

In addition to angiogenic diseases, there are other conditions where endothelial cell proliferation is pathological or, at least, unwanted. For example, endometriosis is characterized by the abnormal proliferation and positioning of certain endothelial cells which normally line the inner wall of the uterus. Control of the angiogenic process could help to prevent or alleviate endometriosis. Also, prevention of endothelial cell growth in the uterus could be a means of birth control.

Endothelial cell growth is associated with wound healing. This growth is undesirable during extended surgical proceedings and where excessive scar formation may occur. Therefore, a means of controlling endothelial cell proliferation would help prevent or reduce unwanted scar formation.

The mechanism of angiogenesis and endothelial cell proliferation has not been completely characterized. It has been established that mast cells accumulate at a tumor site before new capillary growth occurs; however, mast cells alone cannot initiate angiogenesis. Heparin, a mast cell product, has been shown to significantly stimulate the capillary endothelial cell migration which is necessary for angiogenesis (Folkman, J. [1984] Angiogenesis: Initiation and Modulation. In *Cancer Invasion and Metastasis: Biologic and Therapeutic Aspects*. G. L. Nicolson and L. Milas, eds. Raven Press, New York, pp. 201-208).

Several substances are known to have the capability of inhibiting endothelial cell growth in vitro. One of the most extensively studied inhibitors of endothelial cell growth is protamine, which is a protein found only in sperm. Protamine has been shown to inhibit tumor angiogenesis and subsequent tumor growth (Taylor, S. and J. Folkman [1982] Nature 297:307-312). Protamine's anti-angiogenesis activity has been attributed to its well-known capacity to bind heparin (Taylor and Folkman [1982], supra). Clinical experiments with protamine have not been pursued because of the toxicity associated with protamine injection. Protamine, which is usually isolated from salmon sperm, is known to be antigenic in humans, and anaphylactic reactions to this protein have been observed with secondary exposures.

At least two other compounds have been studied in regard to their heparin-binding activity: platelet factor 4 (PF4) and major basic protein. Major basic protein has demonstrated heparin-binding activity but is of little practical utility because of its high toxicity.

Platelet factor 4 is a well-known protein which has been completely sequenced (Deuel, T. F., R. M. Senior, D. Chang, G. L. Griffin, R. L. Heinrikson, and E. T. Kaiser [1981] Proc. Natl. Acad. Sci. USA 78:4585-4587). It is a 70-residue secretable platelet protein with a molecular weight of approximately 7.8 Kd which is released during platelet aggregation. Although there is evidence of heparin binding activity and some indications of anti-angiogenesis activity (Folkman [1984], supra), PF4 has never been shown to have clinical utility.

A compound which has been described as "oncostatin A," and which appears to be the same, or similar to, native PF4, has been implicated as effecting the growth of tumors (U.S. Pat. Nos. 4,645,828 and 4,737,580; both issued to Twardzik et al.). However, the effects reported in these patents pertain to slowly growing human cancer cells in immunodeficient mice. The results of these experiments cannot be reliably extrapolated to predict the effect of rapidly growing tumors which are native to the host animal. Furthermore, the experiments reported in these patents in no way predict or disclose any angiostatic properties.

Various peptides from PF4 have been purified and their properties studied. None has been shown to have any role in the inhibition of angiogenesis. It is known that the C-13 peptide of PF4 is chemotactic for neutrophils and monocytes (Osterman, D. G., G. L. Griffin, R. M. Senior, E. T. Kaiser, and T. H. Deuel [1982] Biochem. and Biophys. Res. Comm. 107(1):130-135). It is significant to note that the infiltration of monocytes would be expected to stimulate the proliferation and migration of local endothelial cells by the secretion of angiogenic factors. Thus, peptides of PF4 could be expected to stimulate, rather than inhibit, angiogenesis.

In addition to angiostatic properties, PF4 possesses characteristic structural features of the pro-inflammatory proteins interleukin-8 and $\beta$-thromboglobulin and has been shown to be chemotactic for neutrophils and monocytes in vivo (Wolpe and Cerami [1989] the FASEB Journal, 3:2565-2573). This similarity of the structure and activities of PF4 to well characterized pro-inflammatory proteins along with the ubiquitous aggregation of platelets at sites of inflammation suggest that PF4 may be an endogenous mediator of inflammation. Thus, it is anticipated that swelling could accompany the administration of PF4 in vivo.

There is a significant and very long-standing need to locate an effective and non-toxic inhibitor of angiogenesis and endothelial cell proliferation. Angiogenesis plays a major role in the initiation and progression of widespread catastrophic illnesses, including cancer. An effective, non-toxic agent which can be administered locally and/or systemically to treat these illnesses would be highly advantageous and has long eluded identification.

The following table may be helpful in identifying the amino acids of the subject invention:

| Amino acid | Three-letter symbol | One-letter symbol |
|---|---|---|
| Alanine | Ala | A |
| Arginine | Arg | R |
| Asparagine | Asn | N |
| Aspartic acid | Asp | D |
| Asn and/or Asp | Asx | B |
| Cysteine | Cys | C |
| Glutamine | Gln | Q |
| Glutamic acid | Glu | E |
| Gln and/or Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF SUMMARY OF THE INVENTION

This invention concerns the discovery that recombinant PF4 (rPF4) has clinical utility in the treatment of diseases which involve angiogenesis and endothelial cell proliferation. Furthermore, PF4 fragments are demonstrated to be inhibitors of angiogenesis. The ability to inhibit angiogenesis has been found in synthetic peptides corresponding to sequences in PF4 as small as the carboxyterminal 13 amino acids.

A further aspect of the invention is the identification of PF4 analogs (mutants) and fragments which may possess enhanced capabilities to inhibit angiogenesis and endothelial cell proliferation.

A further aspect of the invention is the treatment of angiogenic diseases with a combination of PF4 and an anti-inflammatory agent. Anti-inflammatory agents help to alleviate unwanted swelling, pain, or tissue damage which could accompany the administration of pro-inflammatory compounds.

BRIEF DESCRIPTION OF THE DRAWINGS

FIGS. 1A, B and C shows the DNA and amino acid sequences of native rPF4.

DETAILED DESCRIPTION OF THE INVENTION

Figure 2:
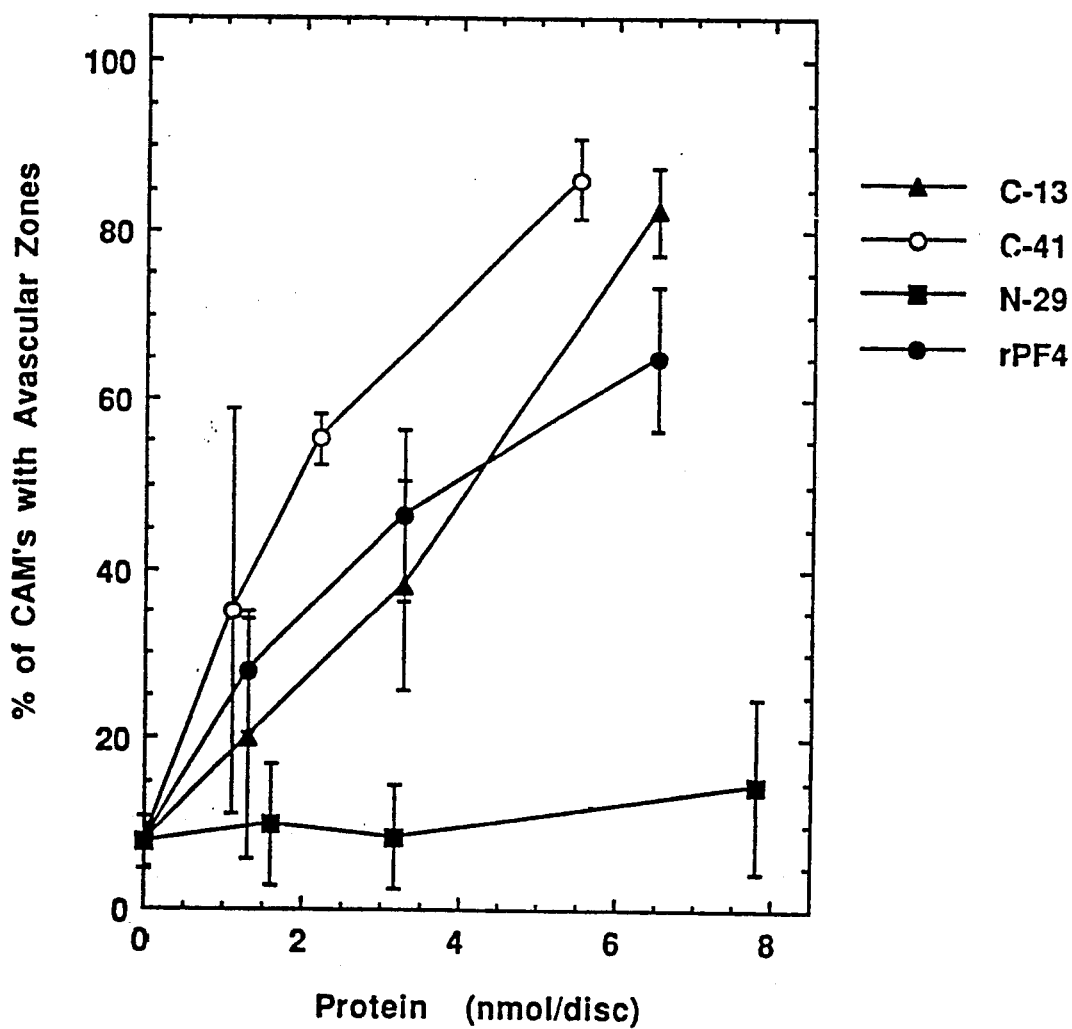
FIG. 2 shows the inhibition of angiogenesis resulting from the treatment of rPF4 and various related peptides.

The subject invention pertains to in vivo inhibition of angiogenesis by rPF4 and certain analogs and peptide fragments of PF4. These analogs and peptide fragments of PF4 can be used to treat angiogenic diseases. As used in this application, the term "angiogenic disease" refers to growth of solid tumors, and other conditions involving angiogenic dysfunctions including diabetic retinopathy, retrolental fibroplasia, neovascular glaucoma, psoriasis, angiofibromas, immune and non-immune inflammation (including rheumatoid arthritis), capillary proliferation in atherosclerotic plaques, hemangiomas, and Kaposi's Sarcoma. The subject invention also concerns the use of rPF4 and PF4 fragments for treatment of diseases of dysregulated endothelial cell proliferation.

The subject invention arises from the unexpected discovery that rPF4 inhibits in vivo capillary formation and embryonic neovascularization. It was also discovered that full length recombinant PF4 inhibits growth factor-dependent human endothelial cell proliferation in vitro.

Significantly, it was also determined that the angiogenesis-inhibiting activity of PF4 was retained by synthetic peptides corresponding to sequences of PF4 as small as 13 amino acids in length. In particular, it was found that a synthetic peptide of 13 amino acids corresponding to the carboxyl terminal portion of PF4 (C-13) displayed potent angiostatic activity.

The finding that PF4 directly inhibits growth of pure cultures of endothelial cells indicates that, advantageously, its effects are not mediated by some other cell type. The finding that PF4 and related peptides inhibit angiogenesis in vivo (CAM assay) and in vitro (endothelial cell proliferation assay) is particularly unexpected in view of PF4's chemotactic activity for monocytes.

The activity of the C-13 peptide is especially surprising in light of its inability to affect the anticoagulant activity of heparin. The use of the C-13 peptide offers several advantages over whole rPF4 such as reduced dosage (weight basis), reduced likelihood of antigenicity, and greater likelihood of effectiveness in novel dosage forms.

The C-13 peptide of PF4 also retains the ability to prevent Con-A induced immunosuppression in mice, an activity which is unaffected by heparin and probably independent of the ability of the peptide to inhibit angiogenesis.

It is well understood that angiogenesis is required for solid tumors to grow beyond a few cubic millimeters. Thus for the treatment of solid tumors, use of rPF4, or a fragment thereof, to cause tumor rejection by inhibiting angiogenesis presents a novel and highly advantageous means of therapy. The fact that the C-13 peptide inhibits angiogenesis without affecting the anticoagulant activity of heparin demonstrates that this small peptide would also have the benefit of not interfering with concurrent anticoagulant therapy. Additionally, small peptides are generally less antigenic than larger proteins, and, thus, the PF4 fragments can be used advantageously for oral and transdermal administration. These types of delivery are particularly useful in the treatment of gastrointestinal capillary proliferation (e.g., Kaposi's Sarcoma) and skin lesions, respectively. Intralesional, as well as systemic, administration of PF4 fragments are also appropriate for treatment of these conditions.

Analogs of PF4 were created which lack heparin binding activity but retain ability to inhibit angiogenesis. One such analog, known as rPF4-241, was created by cassette mutagenesis of a synthetic PF4 gene whereby the DNA sequence encoding the four lysine residues near the carboxy terminus of PF4 were converted to a sequence encoding two Gln-Glu couplets. If rPF4-241 is administered intralesionally, it can be applied such that the dosage is between about 1 μg/lesion and about 4 mg/lesion. For systemic administration, the dosage of rPF4-241 can be between 0.5 mg/kg of body weight and about 100 mg/kg of body weight. Similar and higher dosages can be used for the administration of native sequence rPF4 as well as peptide fragments. For example, dosages of rPF4 and fragments thereof may be twice that of rPF4-241 or higher.

As discussed above, PF4 has been shown to be chemotactic for neutrophils and monocytes in vitro, suggesting that it may mediate an inflammatory response. To assess whether these observations have in vivo relevance, the ability of PF4 to induce acute and chronic dermal inflammation in the mouse was tested. When injected into the murine dermis, recombinant human PF4 (rPF4) induces acute inflammation within two hours, which peaks at about 12 to 18 hours and which resolves by about 36 hours. Injection of an equivalent amount of cytochrome c, buffer alone, or an amino terminal PF4 peptide failed to elicit a significant inflammatory response, however, the carboxy terminal PF4 peptide was pro-inflammatory. The inflammatory infiltrate induced by both rPF4 and the 41 amino acid COOH terminal peptide was composed of neutrophils and to a lesser degree mononuclear cells. Although relatively high concentrations of rPF4 are required to elicit an inflammatory response, these concentrations may be locally obtainable during platelet aggregation or at sites of administration of rPF4 or related compounds.

Advantageously, it was found that the rPF4 pro-inflammatory effect was significantly suppressed by systemic administration of an anti-inflammatory agent without reducing the angiostatic activity.

Materials and Methods

Chicken Chorioallantoic Membrane (CAM) Assay. Fertile eggs were incubated in a stationary position for 3 days at 37° C. and 70-80% relative humidity. During this time, the embryo rose to the upper surface of the egg contents. At the beginning of the 4th day, the eggs were cracked without inversion and carefully deposited into sterile plastic petri dishes such that the embryo remained on the upper surface. The shell-free eggs were incubated for an additional 72 hours at 37° C., under an atmosphere containing 2.5-3.5% $CO_2$ after which the growing embryos developed a recognizable CAM. Discs, made by mixing test samples with 1% (w/v) methylcellulose, were dried and placed on the CAM between major veins and approximately 0.5 cm from the embryo. Following another 48 hour incubation at 37° C. (2.5-3.5% $CO_2$), the samples were scored for their ability to inhibit angiogenesis. Inhibition appears as an avascular zone surrounding the implant and can often include elbows formed by veins avoiding the disc and a reduced number of capillaries in the region of the implant.

Endothelial Cell Proliferation Assay. Human umbilical vein endothelial cells (HUVEC) were cultured in Medium 199 (Gibco) containing 10% (v/v) fetal bovine serum (FBS), 150 mcg/ml endothelial cell growth supplement (ECGS) and 5 units/ml heparin at 37° C. and 4-5% $CO_2$. Every 3-4 days, the cultures were harvested by trypsin treatment, diluted, replated, and grown to confluence. Prior to the start of an experiment, the cells were centrifuged and resuspended in heparin-free media and incubated with the test substance (PF4) for 3 days under standard culture conditions. At the end of the incubation period, the cells were removed by trypsin treatment and counted with a Particle Data Elzone 180 Cell Counter. Statistical significance between means was determined by a standard Student t-test for unpaired data.

Inhibition of DNA synthesis was measured by plating the cells as described, then incubating with the test substance for 24 hours. $^3$H-Thymidine (1μCi/well) was added for an additional 6 hours and the plates were frozen at −70° C. Following 2 freeze/thaw cycles, the cells were aspirated onto a fiber filter, washed with distilled water, fixed with MeOH, and counted for incorporation of radioactivity into DNA.

In vivo Tumor Growth Assay. Normal C57BL/6J female mice (6–8 weeks old) were inoculated subcutaneously with $5 \times 10^5$ log phase cells of a B16-F10 melanoma tumor line. This protocol led to progressive tumor growth resulting in large (300 mm$^3$) necrotic tumors after approximately 10 days, followed by death of untreated animals usually within three weeks of tumor inoculation.

To test the efficacy of rPF4 in preventing in vivo tumor growth and angiogenesis, tumor bearing animals were injected daily, directly into the nascent tumor, with either rPF4 or with buffer lacking rPF4, beginning one day after tumor inoculation. Tumor volume was measured at regular intervals with digital calipers by laboratory personnel uninformed of the specific treatment received by each subject animal.

Footpad Assay. 0.05 ml of PBS containing a test substance was injected intradermally into the right hind footpad of each mouse. An identical amount of diluent, not containing the test substance, was injected into the left hind footpad. At various time points, footpad thicknesses were measured with a spring loaded engineer's micrometer (Fowler Co., Biggswald, England).

At various time points, mice were sacrificed and footpad tissue was prepared for light microscopy. This tissue was used to quantify infiltrating cell types. Biopsy specimens were fixed in 10% buffered formalin for at least 48 hours and then prepared using standard techniques of paraffin embedding and staining with hematoxylin and eosin. Using an ocular grid, four cellular areas of dermis in each specimen were examined in a coded fashion at 1000X magnification and inflammatory cells were quantified. Differences between groups were assessed by Student's t test or analysis of variance, where appropriate.

rPF4 Production. Recombinant PF4 was produced in E. coli as an N-terminal fusion protein containing a unique methionine residue immediately preceding the PF4 portion. More specifically, expression plasmid pPF4-211 was constructed by cloning a synthetic gene encoding native sequence PF4 (FIG. 1) (Poncz et al. [1987] Blood 69:219) into the multiple restriction site region of plasmid pREV2.2 (deposited Jul. 30, 1986; accession #NRRL B-18091). Codon usage in the synthetic gene was optimized for expression in *E. coli*, and synthetic DNA linkers were included on each end to facilitate the directional insertion of the PF4 gene into the vector. The restriction sites HindIII and SmaI were chosen for insertion into pREV2.2. The resulting construct, pPF4-211, expressed a fusion protein containing 34 amino acids of *E. coli* β-glucuronidase (BG) separated from the PF4 sequence by a unique methionine residue.

Cells expressing the fusion protein were subjected to lysozyme (1 mg/g cells), DNase I (500 units/100 g cells) and bead mill treatments. The lysis pellet containing the fusion protein was treated with CNBr (10 g/100 g cells) in 70% formic acid to cleave the fusion protein at the methionine between the BG and PF4 portions. Following evaporation of the CNBr/formic acid, the recombinant protein was extracted with 200 ml of 50 mM Tris-Cl, pH 7.6, 5 mM EDTA, and 10 mM DTT per 100 g of cell starting material. Native sequence rPF4-211 was purified by binding the protein to heparin agarose, removing contaminating proteins with 0.6M NaCl, and eluting with 1.2M NaCl. The resulting material was dialyzed into 20 mM sodium acetate, pH 4.0, and analyzed on a 15% SDS-PA gel stained with Coomassie Brilliant Blue. Minor contaminants could be removed using $C_4$ reverse phase high pressure liquid chromatography (HPLC) to prepare the protein for in vivo use.

Production of rPF4-241 and other PF4 analogs. A synthetic gene encoding the mutant designated rPF4-241 was constructed by changing the codons for the four lysine residues near the C-terminus of PF4 to sequences encoding two Gln-Glu couplets (CAA GAA) by cassette mutagenesis between the BbeI and SmaI sites. Linkers were included at the ends of the synthetic gene, and the gene was inserted into pREV2.2 as described above. Genes encoding other PF4 mutants or analogs were prepared in a similar manner.

The mutant proteins (e.g., rPF4-241) were cleaved and extracted as described above. The extracts were then purified using DEAE-Sepharose chromatography, and eluted with a gradient of 0–1M NaCl. The PF4 proteins generally eluted at approximately 0.5M NaCl and were dialyzed into 20 mM phosphate buffer, pH 7.5. The samples were further purified by reverse phase HPLC.

PF4 peptides. Peptides were prepared by standard solid phase synthesis procedures, cleaved from the solid support and deblocked, and purified by reverse phase HPLC.

Reagents. Recombinant human IL-1 (rIL-1) was purchased from Genzyme Corporation (Cambridge, Mass.). Cytochrome c and *E. coli* endotoxin were purchased from Sigma Chemical Co. (St. Louis, Mo.). Slow release indomethacin pellets were purchased from Innovative Research (Toledo, Ohio).

Mice. C57Bl/6J, A/J and C3H/HeJ female mice, 6-8 weeks old, were purchased from the Jackson Laboratory (Bar Harbor, Me.).

Following are examples which illustrate procedures, including the best mode, for practicing the invention. These examples should not be construed as limiting. All percentages are by weight and all solvent mixture proportions are by volume unless otherwise noted.

EXAMPLE 1

Chicken eggs, prepared as described above, were treated with discs containing several concentrations of recombinant PF4 or peptides derived from the sequence of PF4, rPF4 and C-terminal peptides as small as 13 amino acids inhibited angiogenesis on the CAM (FIG. 2). In each case, the inhibition was dose-dependent and the response approximately equivalent (molar basis) for the inhibitors containing the C-terminal region of PF4. An N-terminal peptide of PF4 (N-29) did not inhibit angiogenesis even at the highest concentration tested, suggesting that all of the anti-angiogenic activity of PF4 is probably associated with the C-terminal portion of the molecule. Since the C-terminus of PF4 is rich in lysine, polylysine was tested in this assay system and found not to cause inhibition at 6.5 nmol dosages.

EXAMPLE 2

The lysine rich region of PF4 (residues 61–66) is also the domain associated with the binding of heparin by PF4. Heparin is known to play a role in modulating angiogenesis, which can also be affected by protamine, another well characterized heparin-binding protein. To assess the ability of PF4-based synthetic peptides to bind heparin, we assayed the activity of coagulation-cascade enzymes which are inhibited by heparin. The Factor Xa assay used here has previously been described in Denton et al. (1983) Biochem. J. 209:455–460. Protamine and platelet factor 4 are able to prevent the heparin inhibition of thrombin and Factor Xa at approximately equimolar concentrations. The 41 amino acid C-terminal peptide of PF4 (C-41) prevented heparin inhibition less effectively, but the C-13 peptide was unable to prevent the inhibition of thrombin even at concentrations ten times that of an effective level of rPF4. This unexpected finding suggests that the C-13 peptide inhibits angiogenesis by some method other than heparin binding.

EXAMPLE 3

Figure 3:
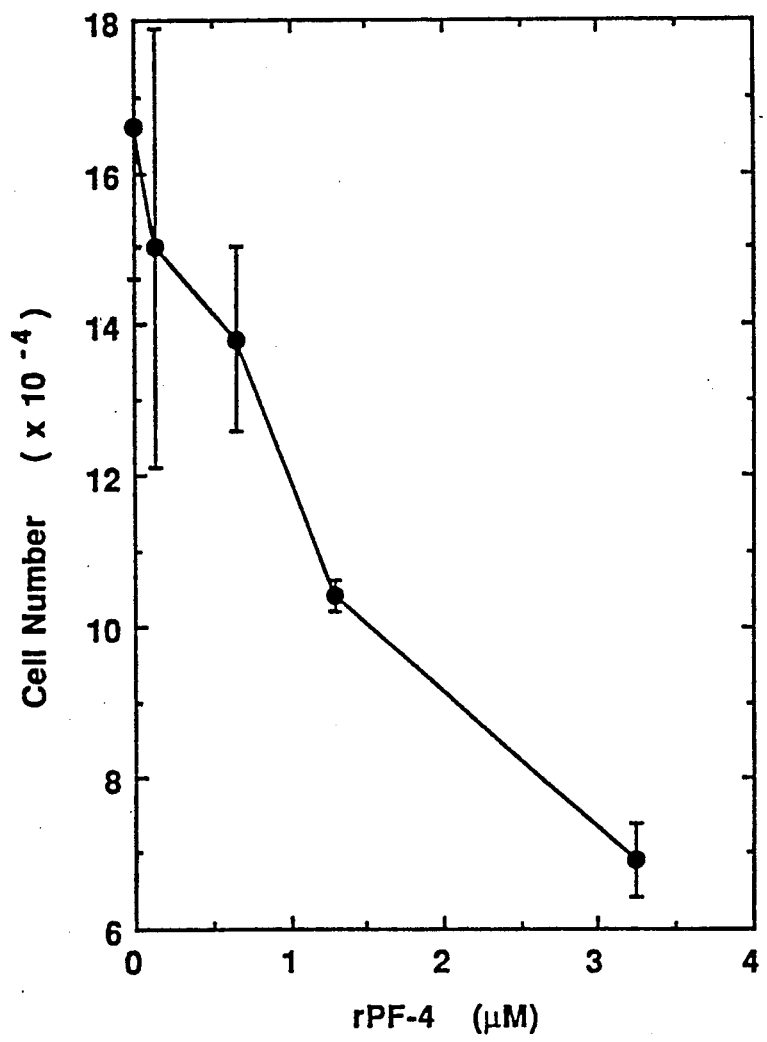
FIG. 3 depicts the inhibition of endothelial cell proliferation by rPF4.

Many angiostatic agents act by direct inhibition of endothelial cell proliferation. Endothelial cell division and growth is tightly controlled and strictly dependent on the presence of growth factors. We evaluated the ability of rPF4 having the wild type sequence (rPF4-211) and related peptides to inhibit growth factor-stimulated human endothelial cell proliferation in vitro. As shown in FIG. 3, rPF4 significantly inhibited endothelial cell growth in a dose-dependent fashion at a concentration as low as 1.3 μM. Inhibition was complete at 3.2 μM in the heparin-deficient medium employed here.

EXAMPLE 4

To assess the importance of the heparin binding activity of PF4 in the inhibition of endothelial cell proliferation, cells were incubated in media containing or lacking 5 units/ml heparin. The presence of heparin stimulated proliferation of these cells during the three day incubation of this experiment. rPF4 significantly inhibited both control (100%) and heparin stimulated (45%) endothelial cell growth (Table 1).

TABLE 1

Attenuation of rPF4 inhibition of endothelial cell growth by heparin.

| Addition | rPF4 | | % Inhibition[a] |
|---|---|---|---|
| | — | 50 mcg/ml | |
| — | 14.4 ± 2.5 | [b]6.0 ± 0.6 | ~100 |
| 5 u/ml heparin | 18.9 ± 1.2 | [b]14.0 ± 0.4 | 45 |

[a]Based on seeding of $8 \times 10^4$ cells/well
[b]Significantly different from appropriate control ($p < 0.005$)

EXAMPLE 5

Construction of rPF4-241

Figure 4:
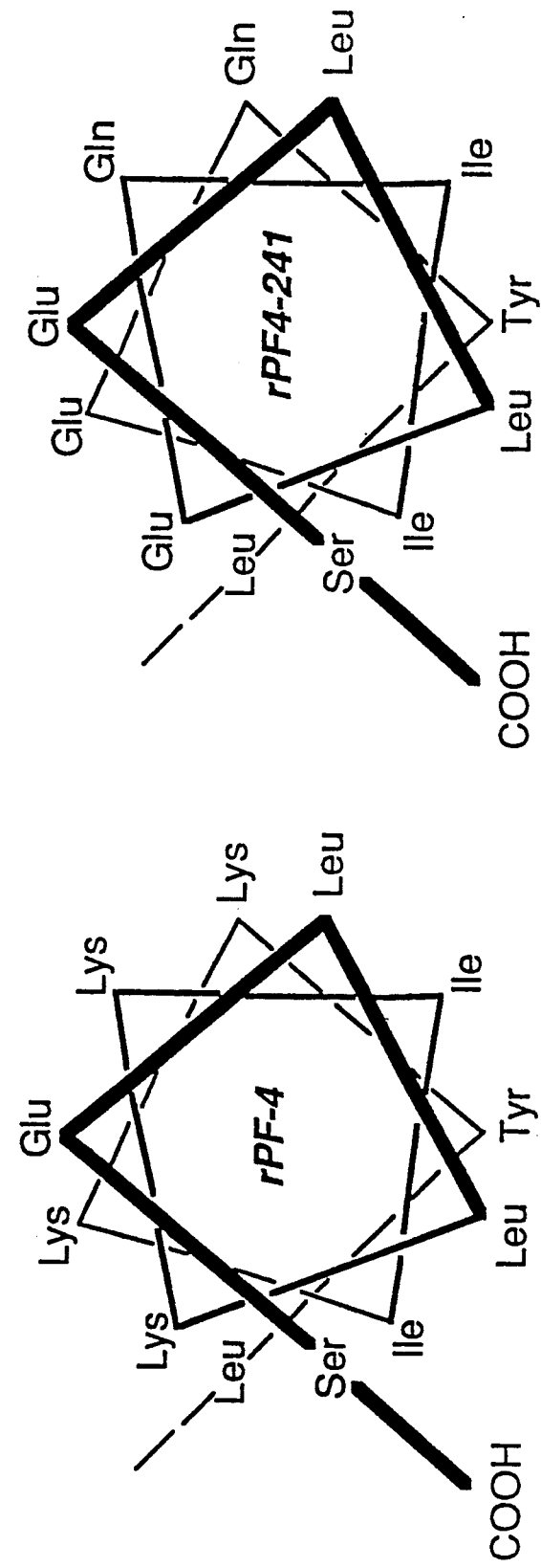
FIG. 4 depicts the alpha-helical configurations of rPF4 and rPF4-241.

A mutant of PF4 was created by converting the four lysine residues at the carboxy terminus of PF4 to two Gln-Glu couplets as disclosed above. This protein apparently retains the alpha-helical secondary structure (FIG. 4) for this region of the molecule with the concurrent loss of heparin binding activity.

The protein was reactive with polyclonal antibodies to native PF4 and was determined to possess the appropriate modifications by amino acid analysis. Significantly, the purified mutant protein lacked heparin-binding activity in the Factor Xa inhibition assay.

The substitutions described here can be made with the peptide fragments as well as with the full length PF4 molecule. For example, C-13-241 has the following sequence:

Pro-Leu-Tyr-Gln-Glu-Ile-Ile-Gln-Glu-Leu-Leu-Glu-Ser

EXAMPLE 6

Inhibition of Angiogenesis by rPF4-241

Figure 5:
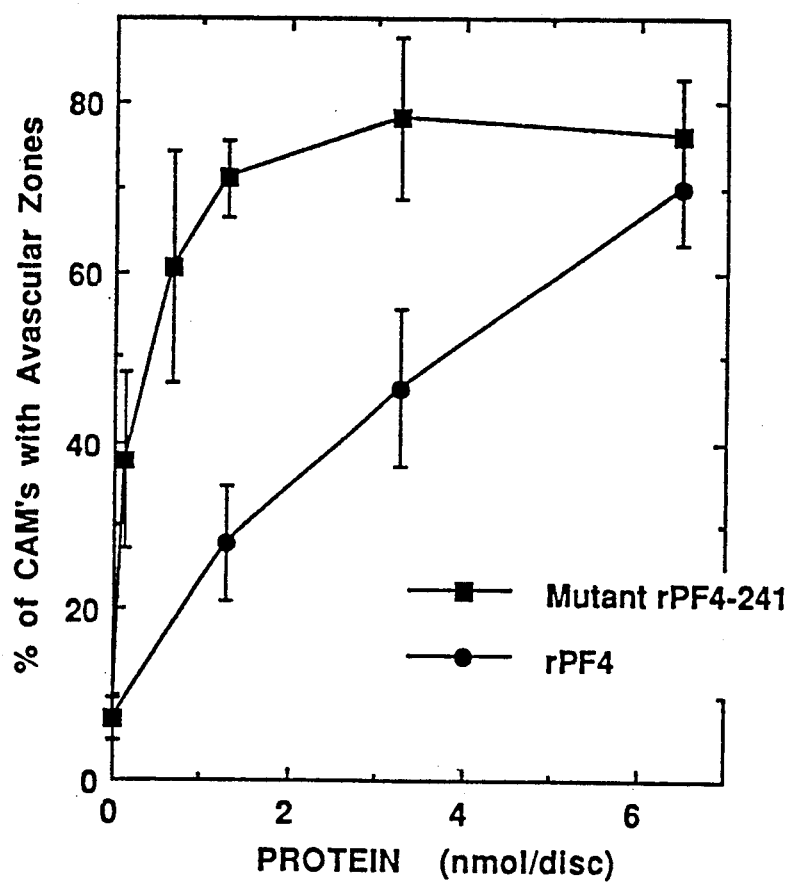
FIG. 5 compares the inhibition of angiogenesis resulting from treatment with rPF4 and rPF4-241.

Purified rPF4-241 was tested for its ability to inhibit capillary growth in the chicken chorioallantoic membrane (CAM) assay. Even at the lowest concentrations tested (1.25 nmol/disc) rPF4-241 extensively inhibited angiogenesis in the CAM system (FIG. 5). This inhibition was even more effective than that caused by equal concentrations of native rPF4 as suggested by larger avascular zones on the membrane. The inhibitory effect of rPF4-241 was not reversed by heparin.

EXAMPLE 7

Inhibition of Human Endothelial Cell Proliferation by rPF4-241

Figure 6:
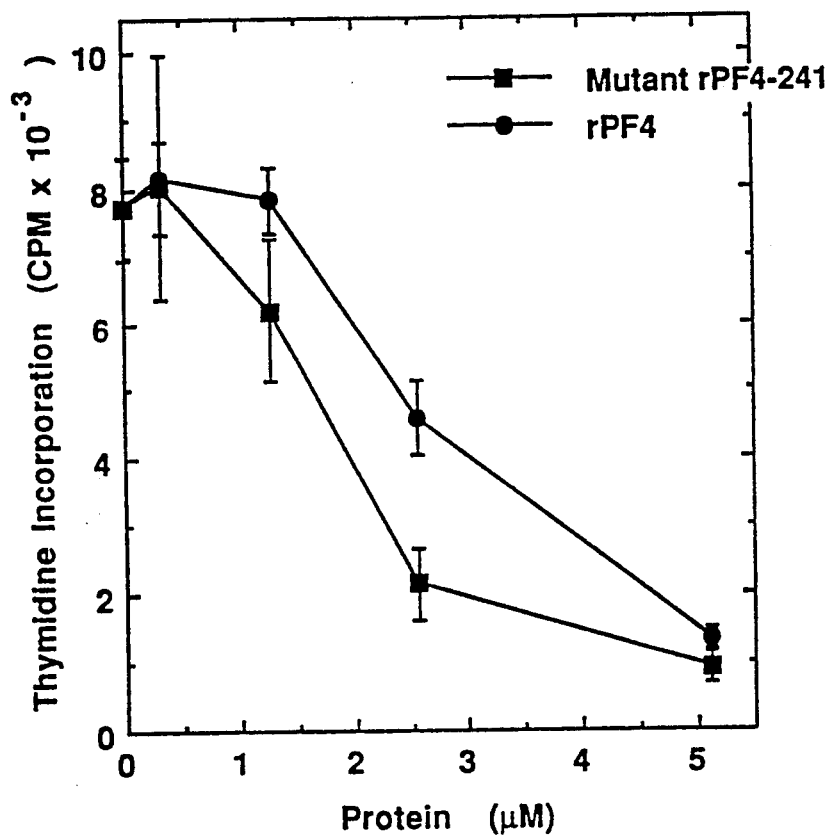
FIG. 6 compares the inhibition of human umbilical vein endothelial cell proliferation resulting from treatment with rPF4 or rPF4-241.

In a test of inhibition of human umbilical vein endothelial cell proliferation by native rPF4 and mutant rPF4-241, both were shown to be effective at inhibiting the proliferation of these cells. The results of this test are shown in FIG. 6.

These results are remarkable in that previous theories of PF4 inhibition of angiogenesis assumed that the PF4 effects were due to heparin binding. We have designed a protein, retaining most of the structural features of native PF4 but lacking detectable heparin binding activity, which may be more active than native PF4 in inhibiting angiogenesis in vivo and endothelial cell proliferation in vitro. Additionally, the mutant we have designed would not be expected to interfere with heparin anticoagulant therapy.

EXAMPLE 8

Inhibition of In Vivo Tumor Growth

Figure 7:
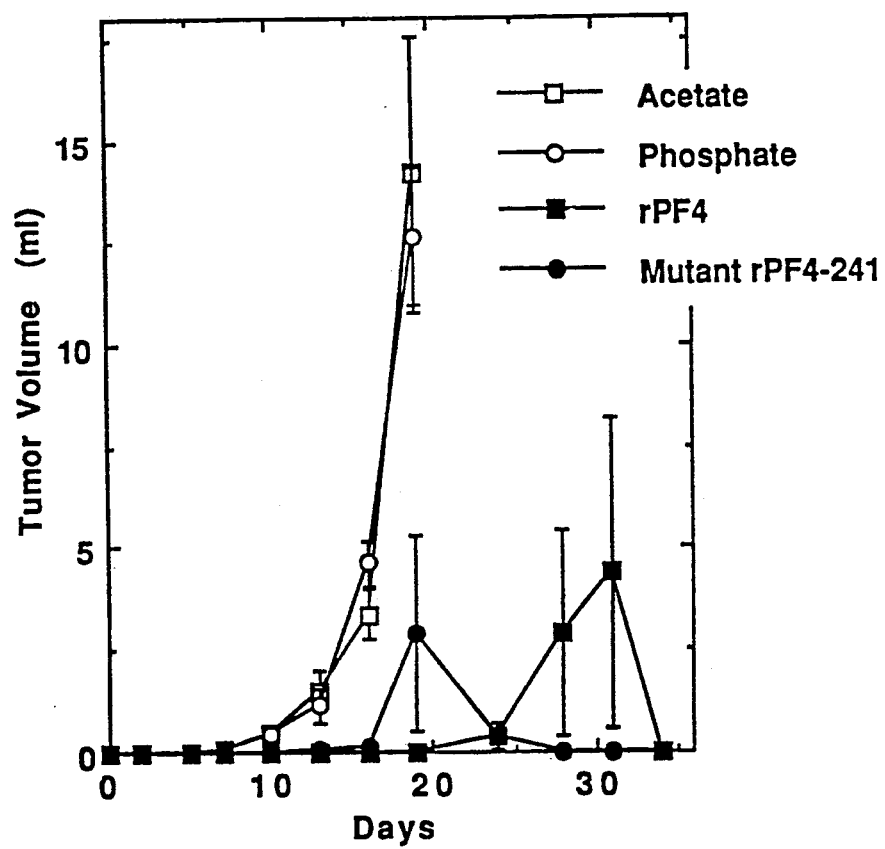
FIG. 7 shows the ability of rPF4 and rPF4-241 to inhibit tumor growth.

The efficacy of rPF4-211 or rPF4-241 in preventing tumor growth and angiogensis was tested. The inhibition of in vivo tumor growth was assayed after injection of either rPF4-211 (in 20 mM NaOAc, pH 4.0) or rPF4-241 (in 50 mM sodium phosphate, pH 6.5, 50 mM NaCl) directly into the nascent tumor, as described in the materials and methods section above. Within seven days of tumor inoculation, animals injected with buffer possessed obvious three dimensional tumors, while rPF4-211-treated animals were essentially tumor-free (FIG. 7). Continued treatment with rPF4 completely suppressed tumor growth under these conditions where control animal tumors became necrotic and large as seen previously with untreated mice. The same effect was observed when rPF4-241 was used as the inhibitory agent.

This finding supports the proposition that rPF4, as an inhibitor of angiogenesis, will possess clinical usefulness in the management of malignant melanoma and other cancers. Progressive growth of tumor growth, but vessel formation which, if inhibited, may not only restrict tumor growth, but stimulate regression of existing vessels, as well as enhance other responses to malignant invasion.

The finding that rPF4 inhibition of in vivo tumor growth was apparent within three days of the initial inoculation (of rPF4) indicates that rPF4 acts to modulate tumor growth by local mechanisms rather than by immunomodulation which would require a longer time course. Additionally, rPF4 did not directly inhibit tumor cell growth in vitro. It appears, therefore, that rPF4 modulated the host's angiogenic response to the growing tumor.

EXAMPLE 9

It has been shown that proteins of identified structure and function may be constructed by changing the amino acid sequence if such changes do not significantly alter the protein secondary structure (Kaiser, E. T., and F. J. Kezdy [1984] Science 223:249–255). The subject invention includes other mutants or fragments of the PF4 sequences depicted herein which lack affinity for heparin and exhibit substantially the same or higher angiostatic activity. A preferred region for modification is the lysine rich region near the carboxy terminus corresponding to the heparin binding domain (residues 60–70). As a general rule, amino acids 60 through 70 cannot be eliminated. Also, as a general rule, it is necessary to have at least one charged residue between positions 60 and 70. Maintenance of an amphipathic α-helix in this region does not seem to be necessary, however, an amphipathic structure may be preferable. Thus, the subject invention includes mutants of the amino acid sequences depicted herein which do not alter the protein secondary structure, or if the structure is altered, the biological activity is retained. In particular it should be understood that conservative substitutions of amino acids may be made. For example, amino acids may be placed in the following classes: basic, hydrophobic, acidic, polar, and amide. Substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Example of Amino Acids |
| --- | --- |
| Basic | K, R, H |
| Hydrophobic | A, L, I, V, P, F, W, Y, M |
| Acidic | E, D |
| Polar | S, T, N, Q, C |
| Amine | Q, N |

In some instances, non-conservative substitutions can also be made. For example, a lysine residue near the C-terminus of PF4 may be replaced with any of the following amino acids: E, Q, D, N, M, A, L, and I. The critical factor is that these substitutions must not significantly detract from the biological activity of the rPF4 or the rPF4 fragment.

We have conducted experiments whereby amino acid substitutions have been made, and the resulting rPF4 mutants have been tested for biological activity. Various mutants which have been constructed are shown in Table 3.

TABLE 3

| Designation | Sequence |
| --- | --- |
| | 60                     70 |
| rPF4-211 | [PF4 AA 1-57] - P L Y K K I I K K L L E S |
| rPF4-231 | [PF4 AA 1-57] - P L Y |
| rPF4-241 | [PF4 AA 1-57] - P L Y Q E I I Q E L L E S |
| rPF4-302 | [PF4 AA 1-57] - P L Y Q Q I I Q Q L L E S |
| rPF4-303 | [PF4 AA 1-57] - P L Y K K Q E K K Q E E S |
| rPF4-307 | [PF4 AA 1-57] - P L Y Q I E I Q L E L E S |
| rPF4-308 | [PF4 AA 1-57] - P L Y N D I I N D L L E S |
| rPF4-315 | [PF4 AA 1-57] - P L Y G E I I G E L L E S |

Results from experiments testing the biological activity of these peptides are shown in Table 4.

TABLE 4

|  | CAM | HUVEC |
| --- | --- | --- |
| rPF4-211 | + | + |
| rPF4-231 | +/− | − |
| rPF4-241 | + + | + |
| rPF4-302 | +/− | − |
| rPF4-303 | + | NA |
| rPF4-307 | + + | + + |
| rPF4-308 | + | NA |
| rPF4-315 | + | NA |

NA = Not available

The results shown in Table 4 clearly demonstrate that it is possible to make rPF4 mutant which retain the biological activity of rPF4 with respect to inhibition of cell growth in the CAM assay and the HUVEC assay. Two of these peptides (rPF4-241 and rPF4-307) exhibited enhanced activity in these assays. The mutants described here are amino acid sequences which are largely homologous with wild type rPF4 (rPF4-211), but which have certain amino acid substitutions. These substitutions were made between amino acids 60 and 70.

Although most of the resulting compounds still exhibit biological activity in the CAM and HUVEC assays, they do not bind heparin. rPF4-302, which does not exhibit significant activity in either the CAM or the HUVEC assay, has no charged amino acid residues between residues 60 and 70. rPF4-231, which also does not exhibit significant biological activity, terminates at amino acid number 60. If a person skilled in the art wished to investigate the biological activity of other rPF4 mutants, it would now be a straightforward procedure to make the desired mutations and test the resulting peptides for activity. Using the teachings of this document, the researcher could prepare and readily test peptides which could be expected to have the desired properties. For example, the amino acid substitutions just described for the full length rPF4 molecule can also be made with the C-13 and C-41 fragments which are described above.

EXAMPLE 10

Inflammatory Properties of rPF4 and Related Compounds

Figure 8:
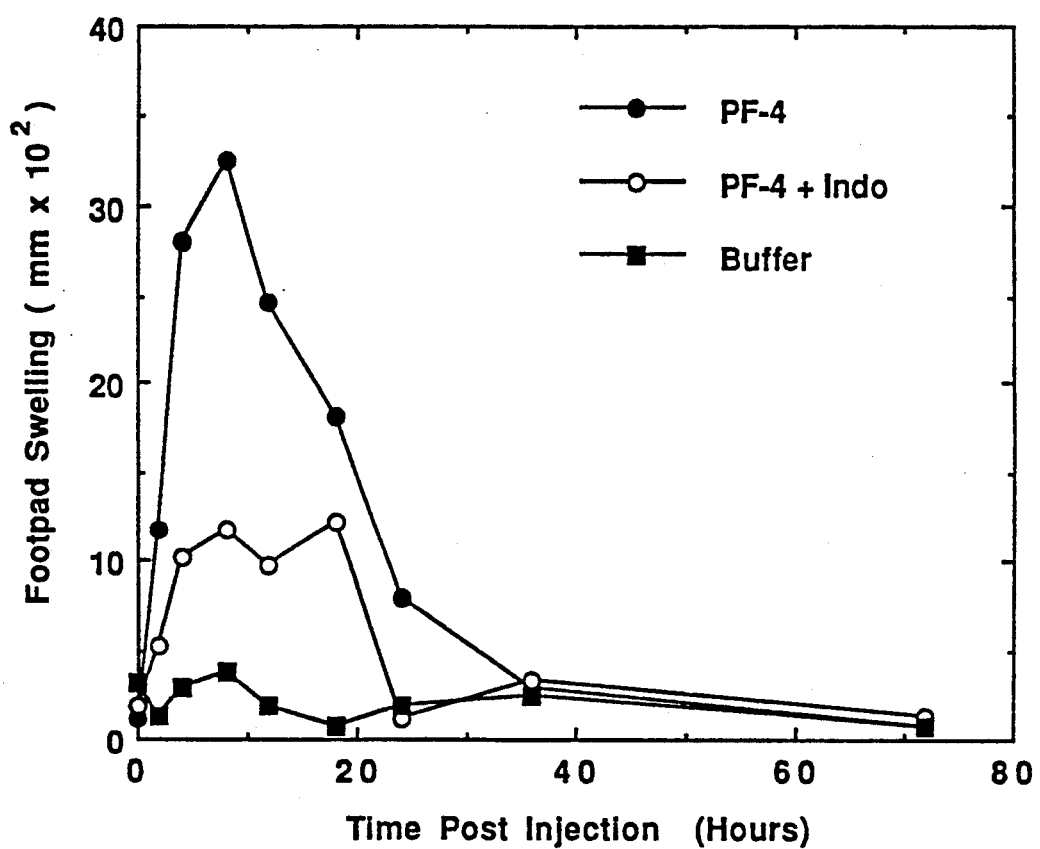
FIG. 8 shows footpad swelling in mice as a function of time after injection with either rPF4, rPF4 and indomethacin, or a buffer solution.
Figure 9:
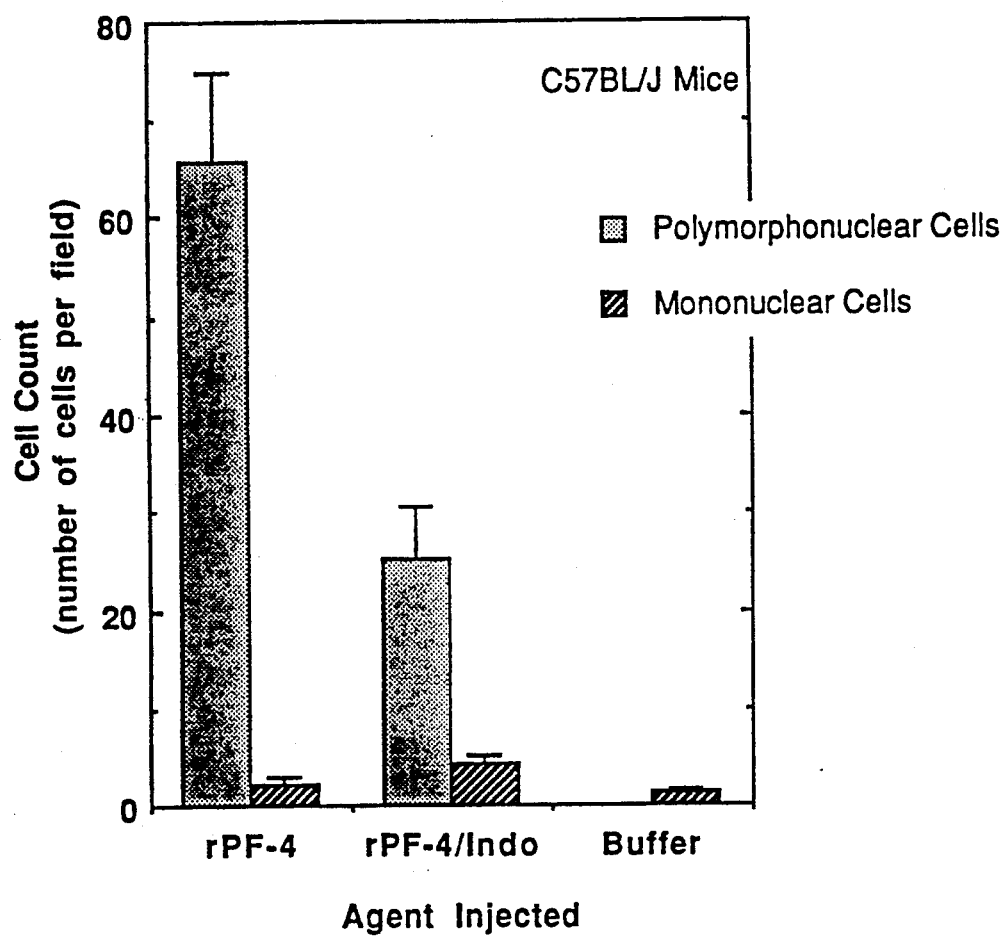
FIG. 9 shows quantification of inflammatory cell infiltrate after treatment with rPF4 or rPF4 with indomethacin.

The inflammatory properties of rPF4 and related compounds were assessed using the footpad assay as described above. At 8 hours, local injection of 25 μg of rPF4-211 into the murine dermis resulted in a brisk inflammatory response as measured by footpad swelling (FIG. 8) and quantification of inflammatory cell infiltrate (FIG. 9). At higher doses the tissue edema does not increase further and may even drop off slightly. It has been found that relatively high local concentrations of PF4 are required to exert a pro-inflammatory effect. Although a brisk inflammatory response occurs with 25 μg of PF4 injected into the murine dermis, at 0.25 μg, the inflammatory response is minimal. The time course of rPF4 induced acute inflammation is broad and resolves by about 36 hours (FIG. 8).

The time course of rPF4 induced inflammation shows a rapid increase from baseline and peaks at between 6 and 12 hours and almost completely resolves by 36 hours.

EXAMPLE 11

Effects of Ant-Inflammatory Agent with rPF4

For each mouse, 0.05 mg, slow release indomethacin pellets (Innovative Research, Toledo, Ohio) were implanted subcutaneously under light ether anesthesia 48 hours prior to an experiment. These pellets continuously release their contents over 14 days.

Systemic treatment of animals with indomethacin significantly blunts the rPF4 pro-inflammatory response (FIG. 8). The area under the curve of footpad swelling in the rPF4 plus indomethacin treated mice is 45.7% of the area under the curve of the rPF4 alone treated mice. The inflammatory cell infiltrate is also partially abrogated with indomethacin treatment. The results of these experiments are summarized in Table 5.

TABLE 5

| | Pro-inflammatory response | |
| --- | --- | --- |
| Treatment | Swelling | Infiltrating |
| rPF4 | + + | + + |
| C-41 | + + | + + |
| N-29 | − | − |
| rPF4-241 | + | + |
| rPF4/indomethacin | +/− | +/− |

Thus, indomethacin can be used to decrease the swelling which could accompany the administration of PF4 or PF4-related substances. Other non-steroidal anti-inflammatory agents could also be used. The anti-inflammatory agents useful in the combinations and methods of this invention include steroidal and non-steroidal anti-inflammatory agents. The non-steroidal anti-inflammatory agents include, but are not limited to, acetyl salicylic acid (aspirin), methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, ketoprofen, and other compounds. Other anti-inflammatory agents useful in the combinations and methods of this invention are lipocortins derived from natural sources or lipocortins and lipocortin-like polypeptides produced by recombinant techniques (see U.S. patent applications Ser. Nos. 690,146; 712,376; 765,877 and 772,892; Wallner, B. et al. [1986] Nature 320:77-81) and uromodulin (Muchmore, A. V., and J. M. Decker [1985] Science 229:479-481), or cyclosporin and its derivatives. Steroidal anti-inflammatory agents which could be used according to the subject invention include, but are not limited to, hydrocortisones.

EXAMPLE 12

Anti-Tumor Activity of rPF4 Combined with Indomethacin

Four groups of mice were used in this experiment. In two groups of mice, slow release indomethacin pellets (50 $\mu$g) were implanted surgically under the skin of the left flank. The other two groups were not treated with indomethacin. Tumors were implanted subcutaneously in all four groups in the right flank.

Figure 10:
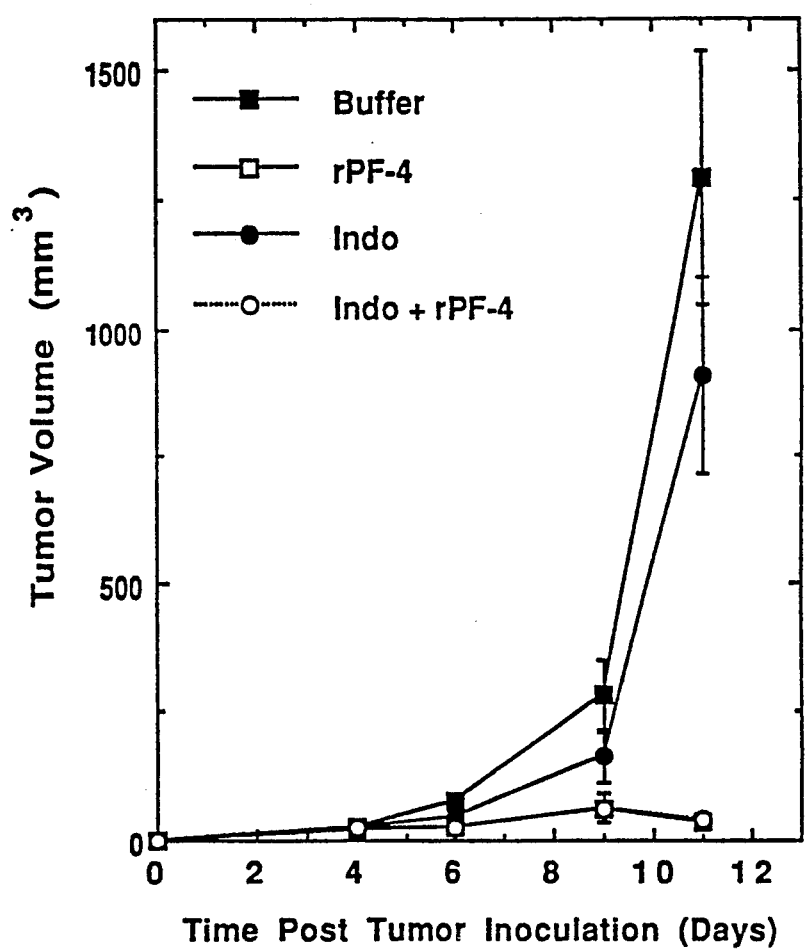
FIG. 10 shows tumor growth after administration of rPF4 alone, indomethacin alone, buffer alone, or rPF4 and indomethacin.

As shown in FIG. 10, the addition of indomethacin to PF4 did not compromise the antitumor activity of PF4. Implanted tumors grew rapidly after day 6 when the tumor was treated with either buffer alone or indomethacin alone. By contrast, the tumors grew very little, if at all, when treated with PF4 or a combination of PF4 and indomethacin.

From these results it is apparent that PF4 retains its antitumor activity even when combined with the anti-inflammatory agent indomethacin.

EXAMPLE 13

Administration of PF4 and Anti-Inflammatory Agents

The combinations and methods of the present invention may allow the administration of PF4, or related compounds, in higher doses in some cases than those tolerated in conventional treatment regimes based upon PF4 alone. Accordingly, the combinations and methods of this invention advantageously reduce or eliminate the inflammatory effects of high dose treatments with PF4 alone. Thus, the use of PF4 in combination with an anti-inflammatory agent may reduce the duration of treatment which would be required by therapies based upon conventionally tolerated lower dosages of PF4 alone.

The combinations and methods of this invention are useful in treating any mammal, including humans. According to this invention, mammals are treated with pharmaceutically effective amounts of the two active components—PF4 and an anti-inflammatory agent—of the combinations of this invention for a period of time sufficient to inhibit angiogenesis or endothelial cell proliferation.

In accordance with this invention, pharmaceutically effective amounts of an anti-inflammatory agent and the PF4 (or PF4-related compounds) are administered sequentially or concurrently to the patient. The most effective mode of administration and dosage regimen of PF4 and anti-inflammatory agent will depend upon the type of disease to be treated, the severity and course of that disease, previous therapy, the patient's health status, and response to PF4 and the judgment of the treating physician. PF4 may be administered to the patient at one time or over a series of treatments.

Preferably, the anti-inflammatory agent and the PF4 are administered sequentially to the patient, with the anti-inflammatory agent being administered before, after, or both before and after treatment with PF4. Sequential administration involves treatment with the anti-inflammatory agent at least on the same day (within 24 hours) of treatment with PF4 and may involve continued treatment with the anti-inflammatory agent on days that the PF4 is not administered. Conventional modes of administration and standard dosage regimens of anti-inflammatory agents may be used (see Gilman, A. G. et al. [eds.] *The Pharmacological Basis of Therapeutics*, pp. 697–713, 1482, 1489–91 [1980]; *Physicians Desk Reference*, 1986 Edition). For example, indomethacin may be administered orally at a dosage of about 25–50 mg, three times a day. Higher doses may also be used. Alternatively, aspirin (about 1500–2000 mg/day), ibuprofen (about 1200–3200 mg/day), or conventional therapeutic doses of other anti-inflammatory agents may be used. Dosages of anti-inflammatory agents may be titrated to the individual patient.

According to one embodiment of this invention, the patient may receive concurrent treatments with the anti-inflammatory agent and PF4. Local, intralesional, or intravenous injection of PF4 is preferred (see Gilman et al., supra at pp. 1290–91). The anti-inflammatory agent should preferably be administered by subcutaneous injection, subcutaneous slow-release implant, or orally.

Alternatively, the patient may receive a composition comprising a combination of PF4 (or PF4-related compounds) and an anti-inflammatory agent according to conventional modes of administration of agents which exhibit anticancer, antitumor, or anti-inflammatory activity. These include, for example, parenteral, subcutaneous, intravenous, or intralesional routes of administration.

The compositions used in these therapies may also be in a variety of forms. These include, for example, solid, semi-solid, and liquid dosage forms, such as tablets, pills, powders, liquid solutions or suspension, liposomes, suppositories, injectable and infusable solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

PF4, or related compounds, may be administered to the patient in any pharmaceutically acceptable dosage form, including intravenous, intramuscular, intralesional, or subcutaneous injection. An effective dose may be in the range of from about 0.01 to about 1.0 mg/kg body weight, it being recognized that lower and higher doses may also be useful. More particularly, doses of PF4 higher than those typically tolerated in patients treated with PF4 alone may advantageously be used in the methods and compositions of the invention. It should, of course, be understood that the compositions and methods of this invention may be used in combination with other therapies.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of inhibiting tumor growth in a mammal having metastatic cancer wherein said method comprises the systemic injection, at a location other than the site of said metastatic cancer, of a composition comprising essentially pure rPF4 wherein said composition is injected at a rate which delivers an angiogenesis-inhibiting amount of rPF4 activity at the site of said metastatic cancer.

2. The method, according to claim 1, wherein said rPF4 is administered at a rate of between about 0.5 mg/kg body weight per day and about 200 mg/kg body weight per day.

3. The method, according to claim 1 or 2, wherein the mode of said systemic administration is selected from the group consisting of intravascular, subcutaneous, and intraperitoneal.

4. The method, according to claim 1, wherein said metastatic cancer is selected from the group consisting of lung tumors, liver tumors, and tumors which produce lung or liver metastases.

* * * * *